US011723701B2

(12) United States Patent
Finley

(10) Patent No.: US 11,723,701 B2
(45) Date of Patent: *Aug. 15, 2023

(54) COMPRESSION FORCE MAGNIFIER

(71) Applicant: Zimmer, Inc., Warsaw, IN (US)

(72) Inventor: Adam Finley, Winona Lake, IN (US)

(73) Assignee: Zimmer, Inc., Warsaw, IN (US)

(*) Notice: Subject to any disclaimer, the term of this patent is extended or adjusted under 35 U.S.C. 154(b) by 162 days.

This patent is subject to a terminal disclaimer.

(21) Appl. No.: 17/106,958

(22) Filed: Nov. 30, 2020

(65) Prior Publication Data

US 2021/0106366 A1 Apr. 15, 2021

Related U.S. Application Data

(63) Continuation of application No. 15/978,071, filed on May 11, 2018, now Pat. No. 10,869,702.

(60) Provisional application No. 62/505,418, filed on May 12, 2017.

(51) Int. Cl.
*A61B 17/80* (2006.01)
*A61B 17/86* (2006.01)
*A61B 17/88* (2006.01)
*A61B 17/56* (2006.01)
*A61B 17/00* (2006.01)

(52) U.S. Cl.
CPC ...... *A61B 17/8014* (2013.01); *A61B 17/8019* (2013.01); *A61B 17/8061* (2013.01); *A61B 17/8605* (2013.01); *A61B 17/8695* (2013.01); *A61B 17/8869* (2013.01); *A61B 17/8033* (2013.01); *A61B 2017/0042* (2013.01); *A61B 2017/565* (2013.01)

(58) Field of Classification Search
CPC ............ A61B 17/8014; A61B 17/8061; A61B 17/8019; A61B 17/8695; A61B 17/8033; A61B 17/8047; A61B 17/8869; A61B 2017/564; A61B 2017/565
USPC ..................... 606/70–71, 280, 282, 286, 288
See application file for complete search history.

(56) References Cited

U.S. PATENT DOCUMENTS

| 3,528,085 A | 9/1970 | Reynolds, Jr. |
| 3,779,240 A | 12/1973 | Kondo |
| 3,866,607 A | 2/1975 | Forsythe et al. |
| 4,388,921 A | 6/1983 | Sutter et al. |
| 4,705,031 A | 11/1987 | Wolter |

(Continued)

FOREIGN PATENT DOCUMENTS

| AU | 2019280104 A1 | 7/2020 |
| CN | 106236228 A | 12/2016 |

(Continued)

OTHER PUBLICATIONS

UK Search Report dated Jun. 12, 2020 based on GB 1918520.6 (1 p.).

(Continued)

*Primary Examiner* — Marcela I. Shirsat
(74) *Attorney, Agent, or Firm* — Schwegman Lundberg & Woessner, P.A.

(57) ABSTRACT

A compression force magnifier comprising: an engaging surface for attaching to a bone plate; a ramped component above the engaging surface, the ramped component having a bottom surface adjacent the engaging surface and an angled upper surface; and a hole extending through the ramped component and the engaging surface.

15 Claims, 24 Drawing Sheets

(56) References Cited

U.S. PATENT DOCUMENTS

| | | | |
|---|---|---|---|
| 4,957,496 A * | 9/1990 | Schmidt | A61B 17/8014 |
| | | | 606/70 |
| 5,486,176 A | 1/1996 | Hildebrand et al. | |
| 5,643,265 A | 7/1997 | Errico et al. | |
| 6,533,786 B1 | 3/2003 | Needham et al. | |
| 6,723,098 B1 | 4/2004 | Shah | |
| 8,167,919 B2 | 5/2012 | Foley et al. | |
| 8,257,403 B2 | 9/2012 | Den Hartog et al. | |
| 8,257,406 B2 | 9/2012 | Kay et al. | |
| 8,414,582 B2 | 4/2013 | Overes et al. | |
| 8,747,443 B2 | 6/2014 | Aferzon | |
| 8,852,249 B2 | 10/2014 | Ahrens et al. | |
| D717,433 S | 11/2014 | Samani et al. | |
| 8,888,825 B2 | 11/2014 | Batsch et al. | |
| 8,894,694 B2 | 11/2014 | Brandon | |
| 8,906,075 B2 * | 12/2014 | Conley | A61B 17/8605 |
| | | | 606/282 |
| D728,104 S | 4/2015 | Katchis et al. | |
| 9,204,912 B2 | 12/2015 | Price et al. | |
| 9,414,870 B2 | 8/2016 | Ryan et al. | |
| 9,572,607 B2 | 2/2017 | Johnson et al. | |
| D782,046 S | 3/2017 | Mcquilton | |
| 9,681,896 B2 | 6/2017 | Aferzon | |
| 10,076,377 B2 | 9/2018 | Bonutti et al. | |
| 10,092,336 B2 | 10/2018 | Hess et al. | |
| 10,111,693 B2 | 10/2018 | Kannan et al. | |
| 10,869,702 B2 | 12/2020 | Finley | |
| D927,295 S | 8/2021 | Lanois | |
| 11,202,664 B2 | 12/2021 | Finley | |
| 2004/0117016 A1 | 6/2004 | Abramson | |
| 2005/0187551 A1 | 8/2005 | Orbay et al. | |
| 2008/0015592 A1 | 1/2008 | Long et al. | |
| 2012/0095466 A1 | 4/2012 | Winslow et al. | |
| 2012/0116401 A1 | 5/2012 | Gradl et al. | |
| 2012/0191138 A1 | 7/2012 | Kiester | |
| 2012/0197301 A1 | 8/2012 | Foley et al. | |
| 2012/0197303 A1 | 8/2012 | King et al. | |
| 2014/0243828 A1 | 8/2014 | Heiney | |
| 2014/0277190 A1 | 9/2014 | Splieth et al. | |
| 2015/0250509 A1 * | 9/2015 | Kannan | A61B 17/8004 |
| | | | 606/71 |
| 2016/0128745 A1 | 5/2016 | Sidebotham et al. | |
| 2016/0228167 A1 | 8/2016 | Wahl | |
| 2017/0156768 A1 | 6/2017 | Dresher et al. | |
| 2017/0348033 A1 | 12/2017 | Varner et al. | |
| 2018/0214163 A1 | 8/2018 | McCormick | |
| 2019/0029739 A1 | 1/2019 | Finley | |
| 2020/0187997 A1 | 6/2020 | Finley | |
| 2022/0233221 A1 | 7/2022 | Kay et al. | |
| 2022/0249141 A1 | 8/2022 | Laroche et al. | |
| 2022/0265328 A1 | 8/2022 | Oberli et al. | |

FOREIGN PATENT DOCUMENTS

| | | | |
|---|---|---|---|
| DE | 102019134573 A1 | 6/2020 | |
| EP | 0016338 A1 | 2/1980 | |
| GB | 2582408 A | 9/2020 | |
| GB | 2590571 A | 6/2021 | |
| JP | 2020096835 A | 6/2020 | |

OTHER PUBLICATIONS

"U.S. Appl. No. 15/978,071, Final Office Action dated Jun. 4, 2020", 11 pgs.

"U.S. Appl. No. 15/978,071, Non Final Office Action dated Dec. 10, 2019", 15 pgs.

"U.S. Appl. No. 15/978,071, Notice of Allowance dated Aug. 20, 2020", 10 pgs.

"U.S. Appl. No. 15/978,071, Response filed Mar. 10, 2020 to Non Final Office Action dated Dec. 10, 2019", 10 pgs.

"U.S. Appl. No. 15/978,071, Response filed Jul. 31, 2020 to Final Office Action dated Jun. 4, 2020", 8 pgs.

"U.S. Appl. No. 15/978,071, Response filed Nov. 26, 2019 to Restriction Requirement dated Nov. 8, 2021", 2 pgs.

"U.S. Appl. No. 15/978,071, Restriction Requirement dated Nov. 8, 2021", 7 pgs.

"U.S. Appl. No. 16/222,477, 312 Amendment filed Aug. 31, 2021", 4 pgs.

"U.S. Appl. No. 16/222,477, Final Office Action dated Apr. 29, 2021", 13 pgs.

"U.S. Appl. No. 16/222,477, Non Final Office Action dated Nov. 9, 2020", 9 pgs.

"U.S. Appl. No. 16/222,477, Notice of Allowance dated Aug. 11, 2021", 10 pgs.

"U.S. Appl. No. 16/222,477, Notice of Allowance dated Aug. 23, 2021", 5 pgs.

"U.S. Appl. No. 16/222,477, Preliminary Amendment filed Feb. 26, 2019", 5 pgs.

"U.S. Appl. No. 16/222,477, PTO Response to Rule 312 Communication dated Sep. 2, 2021", 2 pgs.

"U.S. Appl. No. 16/222,477, Response filed Feb. 9, 2021 to Non Final Office Action dated Nov. 9, 2020", 9 pgs.

"U.S. Appl. No. 16/222,477, Response filed Jul. 28, 2021 to Final Office Action dated Apr. 29, 2021", 9 pgs.

"U.S. Appl. No. 16/222,477, Response filed Nov. 3, 2020 to Restriction Requirement dated Oct. 1, 2020", 2 pgs.

"U.S. Appl. No. 16/222,477, Restriction Requirement dated Oct. 1, 2020", 6 pgs.

"United Kingdom Application Serial No. 1918520.6, Examination Report under section 18(3) dated Apr. 19, 2022", 3 pgs.

"United Kingdom Application Serial No. 1918520.6, Response filed Jun. 20, 2022 to Examination Report under section 18(3) dated Apr. 19, 2022", 15 pgs.

"United Kingdom Application Serial No. 1918520.6, Subsequent Examination Report under Section 18 (3) dated Aug. 4, 2022", 3 pgs.

"United Kingdom Application Serial No. 2102810.5, Request for further search fee under Section 18(1A) dated Apr. 19, 2022", 2 pgs.

"United Kingdom Application Serial No. 2102810.5, Response filed Jun. 8, 2022 to Request for further search fee under Section 18(1A) dated Apr. 19, 2022", 1 pg.

"United Kingdom Application Serial No. 2102810.5, Subsequent Examination Report under Section 18 (3) dated Aug. 4, 2022", 5 pgs.

U.S. Appl. No. 15/978,071 U.S. Pat. No. 10,869,702, filed May 11, 2018, Compression Force Magnifier.

U.S. Appl. No. 29/759,388, filed Nov. 23, 2020, Compression Force Magnifier.

U.S. Appl. No. 16/222,477 U.S. Pat. No. 11,202,664, filed Dec. 17, 2018, Compression Force Magnifier.

Orthopedic Plates, [Online] Retrieved from the internet: <https://monib-health.com/en/post/101-different-types-of-orthopedic-plates>, (Jul. 1, 2021), 3 pgs.

Implants Compression Plates, [Online] Retrieved from the internet: <https://www.mdi-llc.net/implants/>, (2023), 3 pgs.

"U.S. Appl. No. 29/759,388, Restriction Requirement dated Feb. 3, 2023", 8 pgs.

"United Kingdom Application Serial No. 1918520.6, Response Filed Oct. 4, 2022 to Subsequent Examination Report under Section 18 (3) dated Aug. 4, 2022", 16 pgs.

"United Kingdom Application Serial No. 2102810.5, Response filed Oct. 13, 2022 Subsequent Examination Report under Section 18 (3) dated Aug. 4, 2022", 14 pgs.

* cited by examiner

COMPRESSION FORCE MAGNIFIER

CROSS REFERENCE

This application is a continuation of U.S. Ser. No. 15/978,071 filed May 11, 2018, entitled "COMPRESSION FORCE MAGNIFIER", which claims priority under 35 U.S.C. § 119 of provisional application U.S. Ser. No. 62/505,418, filed on May 12, 2017, all of which are fully incorporated herein by reference.

This application is also related to U.S. Ser. No. 16/222,477 filed Dec. 17, 2018, entitled "COMPRESSION FORCE MAGNIFIER", the disclosure of which is incorporated by reference herein.

This application is also related to design patent application U.S. Ser. No. 29/759,388 filed Nov. 23, 2020, entitled "COMPRESSION FORCE MAGNIFIER", the disclosure of which is incorporated by reference herein.

BACKGROUND

Field of the Invention

The present invention relates generally to orthopedic implant fixation devices and, more particularly, to an orthopedic bone plate with a compression enhancement feature.

Description of the Related Art

Hallux Abducto Valgus ("HA V") deformity is generally described as a medial deviation of the first metatarsal accompanied by a lateral deviation and/or valgus rotation of the hallux. The result effect is a subluxation of the first metatarsophalangeal joint ("MTPJ") creating a boney prominence on the inside of the foot near the base of the hallux. HAY may lead to painful motion of the hallux joint and/or difficulty fitting footwear. Other conditions associated with HAV may include: hammer toe formation of the adjacent toes, forefoot pain on the ball of the foot (aka metatarsalgia), stress fractures of the adjacent metatarsals, flat feet (pes planus), and arthritis. Misshaped bones (hallux and/or first metatarsal) may also cause bunions. Bunions have long been one of the more common types of painful foot deformities.

Various techniques have been developed to surgically correct HAV. The most basic technique simply involves resecting any enlarged bone at the medial aspect of the first metatarsal head, but this approach is typically used in conjunction with other more advanced techniques. A common technique involves an osteotomy (bone cut) procedure in which the first metatarsal is broken into two pieces and the distal portion of the bone is translated closer (medially) to the adjacent second metatarsal. The osteotomy may be performed at several locations on the first metatarsal depending on the severity of the deformity.

Alternative techniques have been developed that do not require an osteotomy. One such technique is often referred to as the Lapidus approach. In general, the idea behind the Lapidus approach is to permanently fuse the base of the first metatarsal to the medial cuneiform bone in a corrected new position. This permanent fixation is carried out by first reducing the IMA and then fusing the MCJ. Implementation of this approach often involves the use of a plate and screws that attach the plate to the metatarsal and medial cuneiform.

SUMMARY OF THE INVENTION

In one exemplary embodiment, the invention is a compression force magnifier comprising: an engaging surface for attaching to a bone plate; a ramped component above the engaging surface, the ramped component having a bottom surface adjacent the engaging surface and an angled upper surface; and a hole extending through the ramped component and the engaging surface.

In another exemplary embodiment, the invention is a compression force magnifier, said compression force magnifier comprising: a vertical axis; a proximal surface sloped at a predetermined angle relative to said vertical axis; a flat distal surface, said distal surface disposed opposite said proximal surface; an extension member, said extension member extending from said distal surface; a bore, said bore disposed through said body from said proximal surface through said distal surface and said extension member, said extension member adapted to fit into an aperture on a bone plate.

In another exemplary embodiment, the invention is a compression force magnifier, said compression force magnifier comprising: a vertical axis; a proximal surface sloped at a predetermined angle relative to said vertical axis; a flat distal surface, said distal surface disposed opposite said proximal surface; a bore, said bore disposed through said body from said proximal surface through said distal surface; and means for attaching said magnifier to a bone plate.

In another exemplary embodiment, the invention is a bone compression assembly apparatus, said assembly apparatus comprising: a bone plate, said plate having a proximal surface and a bone contacting surface disposed opposite said proximal surface, said bone plate further comprising at least one aperture disposed through said plate between said proximal surface and said bone contacting surface, said aperture having a longitudinal axis; and a compression force magnifier, said compression force magnifier disposed on the proximal surface of said bone plate, said compression force magnifier comprising: a vertical axis; a proximal surface sloped at a predetermined angle relative to said vertical axis; a flat distal surface, said distal surface disposed opposite said proximal surface; an extension member, said extension member extending from said distal surface; a bore, said bore disposed through said body from said proximal surface through said distal surface and said extension member, said extension member connected to said aperture on said bone plate such that the longitudinal axis of said aperture is generally colinear with the longitudinal axis of said bore.

In another exemplary embodiment, the invention is a bone compression assembly apparatus, said assembly apparatus comprising: a bone plate, said plate having a proximal surface and a bone contacting surface disposed opposite said proximal surface, said bone plate further comprising at least one aperture disposed through said plate between said proximal surface and said bone contacting surface, said aperture having a longitudinal axis; and a compression force magnifier, said compression force magnifier comprising: a vertical axis; a proximal surface sloped at a predetermined angle relative to said vertical axis; a flat distal surface, said distal surface disposed opposite said proximal surface; a bore, said bore disposed through said body from said proximal surface through said distal surface; said compression force magnifier attached to said bone plate such said axis of said bore is collinear with said axis of said aperture and said distal surface of said magnifier abuts said proximal surface of said plate.

In another exemplary embodiment, the invention is a bone compression assembly apparatus, said assembly apparatus comprising: a bone plate, said plate having a proximal surface and a bone contacting surface disposed opposite said proximal surface, said bone plate further comprising at least one aperture disposed through said plate between said proximal surface and said bone contacting surface, said aperture having a longitudinal axis; a compression force magnifier, said compression force magnifier comprising: a vertical axis; a proximal surface sloped at a predetermined angle relative to said vertical axis; a flat distal surface, said distal surface disposed opposite said proximal surface; a bore, said bore disposed through said body from said proximal surface through said distal surface; said compression force magnifier attached to said bone plate such said axis of said bore is collinear with said axis of said aperture and said distal surface of said magnifier abuts said proximal surface of said plate; and a screw, said screw having a proximal head having a non-flat bottom, said screw disposed through said bore and said aperture and into a bone.

In another exemplary embodiment, the invention is a bone plate, said plate comprising: an elongated body, said body having a proximal non-bone contacting surface and a distal bone contacting surface disposed opposite said proximal surface; an aperture disposed through said plate, said aperture in communication with said proximal surface and said distal surface of said plate, said aperture comprising a vertical axis; and a compression magnification element, said compression magnification element having a vertical axis, a proximal surface sloped at a predetermined angle relative to said vertical axis, a flat distal surface disposed opposite said proximal surface, and a bore disposed through said compression magnification element from said proximal surface through said distal surface, said compression magnification element disposed on said plate such that said vertical axis of said bore for said compression magnification element is colinear with said vertical axis of said aperture of said plate.

In another exemplary embodiment, the invention is a bone plate, said plate comprising: an elongated body, said body having a first end, a second end, a proximal non-bone contacting surface, and a distal bone contacting surface disposed opposite said proximal surface; an aperture disposed through said plate, said aperture in communication with said proximal surface and said distal surface of said plate, said aperture comprising a vertical axis; and a compression magnification element, said compression magnification element having a vertical axis, a proximal surface sloped at a predetermined angle relative to said vertical axis, a flat distal surface disposed opposite said proximal surface, and a bore disposed through said compression magnification element from said proximal surface through said distal surface, said compression magnification element attached to one of said first and second end of said plate.

In another exemplary embodiment, the invention is a bone compression assembly comprising: a bone plate including a plurality of screw holes; and a compression force magnifier engaged within at least one screw hole, the compression force magnifier comprising: an engaging surface for attaching to a bone plate; a ramped component above the engaging surface, the ramped component having a bottom surface adjacent the engaging surface and an angled upper surface; and a hole extending vertically through the ramped component and the engaging surface.

In another exemplary embodiment, the invention is a method of using a compression force magnifier, the method comprising: attaching a bone plate to a first bone; inserting a compression force magnifier into an opening disposed on a top surface of the bone plate; inserting a first screw into the compression force magnifier and into a second bone; applying a compressive force between the first bone and the second bone; inserting a second screw through a hole in the bone plate into the second bone; removing the first screw and the compression force magnifier; and inserting a third screw, larger than the first screw, into a hole left by the first screw.

BRIEF DESCRIPTION OF THE DRAWINGS

For the purposes of illustrating the compression bone plate apparatus and related methods described herein, there is shown herein illustrative embodiments. These illustrative embodiments are in no way limiting in terms of the precise arrangement and operation of the disclosed compression bone plate apparatus and related methods and other similar embodiments are envisioned within the spirit and scope of the present disclosure.

DETAILED DESCRIPTION

Figure 1:
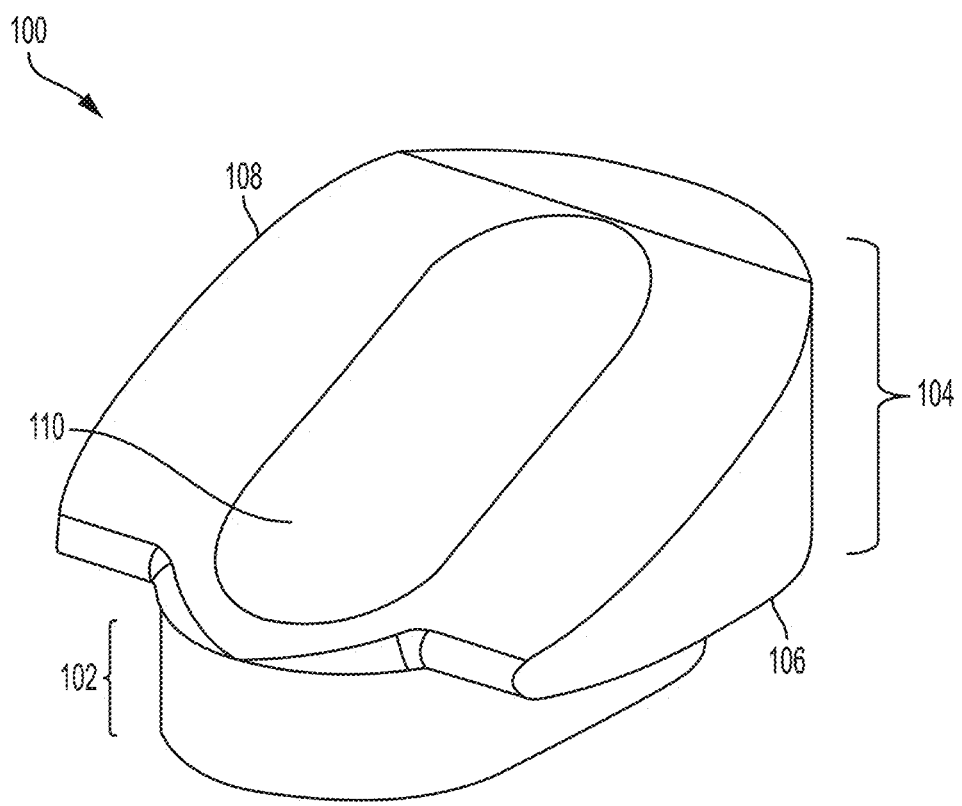
FIG. 1 illustrates a top perspective view of a compression force magnifier, in accordance with an aspect of the present invention.

The term "compression force magnifier" as used herein shall not be interpreted as limited to use on any particular joint, but the phrase may be used for fusion and osteotomy of any type of joint, and further may be used to reduce a joint prior to soft tissue repair.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

As shown in FIGS. 1-5, the embodiments of compression force magnifiers, according to the present disclosure, are disclosed. The compression force magnifier 100 can include an engaging surface 102 for mating with a bone plate, as will be described and illustrated later. The engaging surface 102 can include any means for attaching to, for instance, a screw hole in a bone plate. This can include, for example, but is not limited to an interference tab, which is compressed when inserted into a slot, an interference fit between a screw slot and hole, a tapered fit, a press-fit, a tab for engaging a ridge in a screw slot, or a split bottom which engages the screw slot and causes essentially a friction fit.

As shown in FIGS. 1-5, the compression force magnifier 100 may also include a ramped component 104 positioned above the engaging surface 102. For instance, the ramped component 104 may include a flat bottom surface 106 immediately adjacent to the engaging surface 102 for sitting against a surface of a bone plate. As shown in FIGS. 1-4, the ramped component may also include a pitched, or angled, upper surface 108, creating a ramped surface, the angle of which may vary for example from 1 to 89 degrees, but more preferably in the range of 20 to 55 degrees with a height range for example of generally 1.5 to 5 millimeter.

Figure 2:
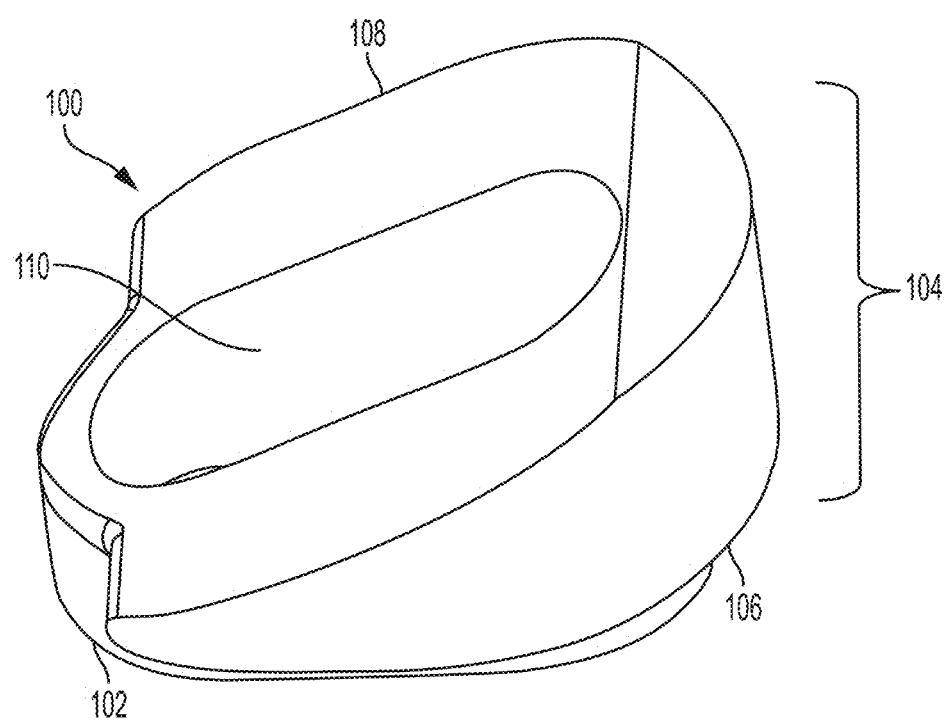
FIG. 2 illustrates a side perspective view of a compression force magnifier, in accordance with an aspect of the present invention.
Figure 3:
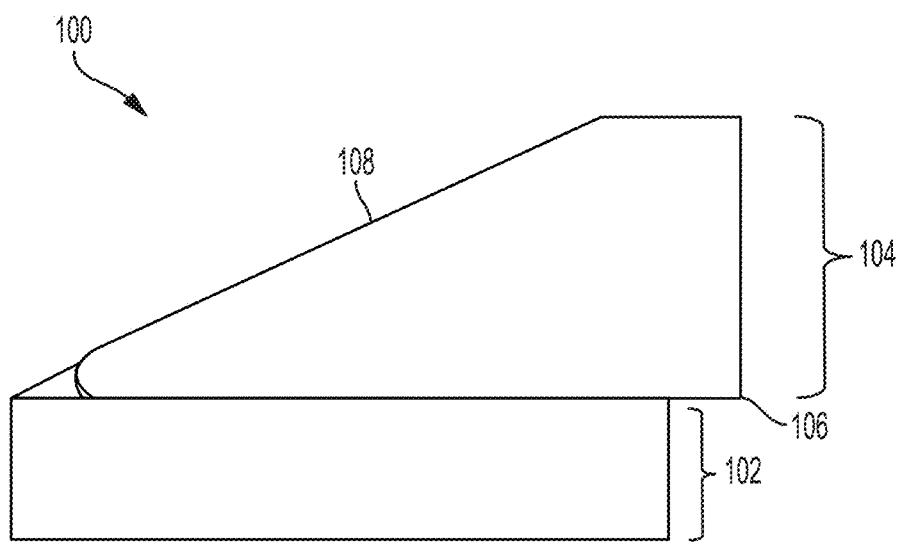
FIG. 3 illustrates a side elevational view of a compression force magnifier, in accordance with an aspect of the present invention.
Figure 4:
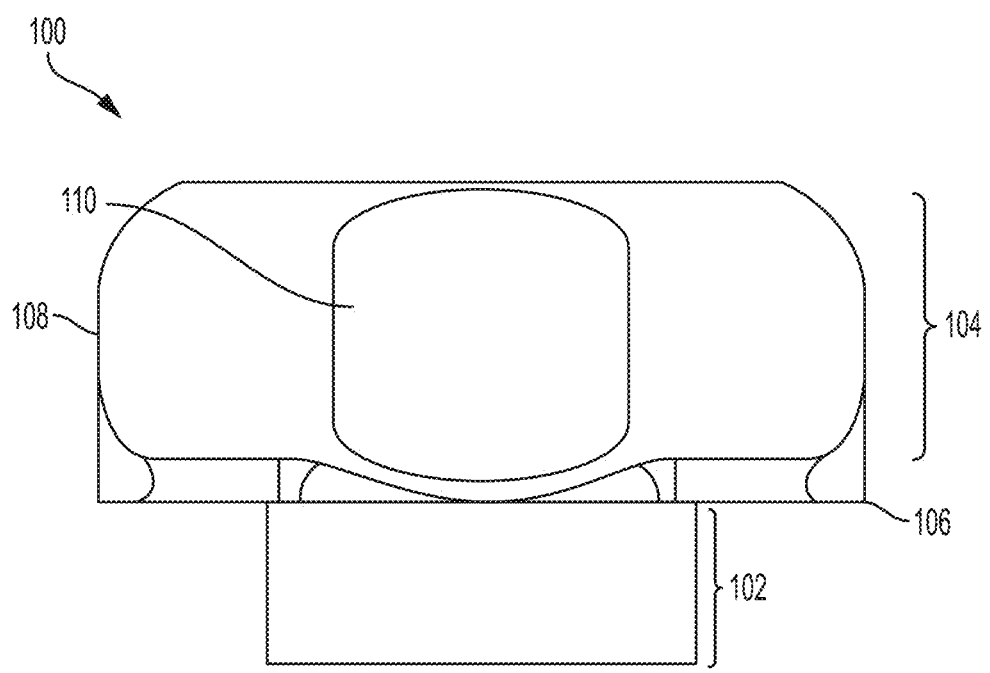
FIG. 4 illustrates a front elevational view of a compression force magnifier, in accordance with an aspect of the present invention.
Figure 5:
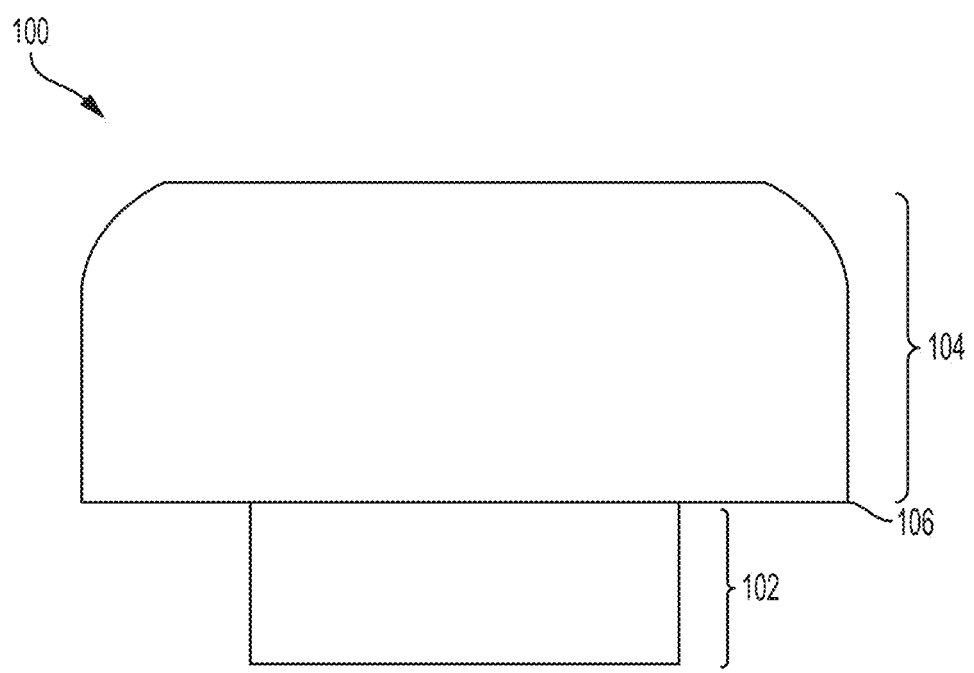
FIG. 5 illustrates a rear elevational view of a compression force magnifier, in accordance with an aspect of the present invention.
Figure 6:
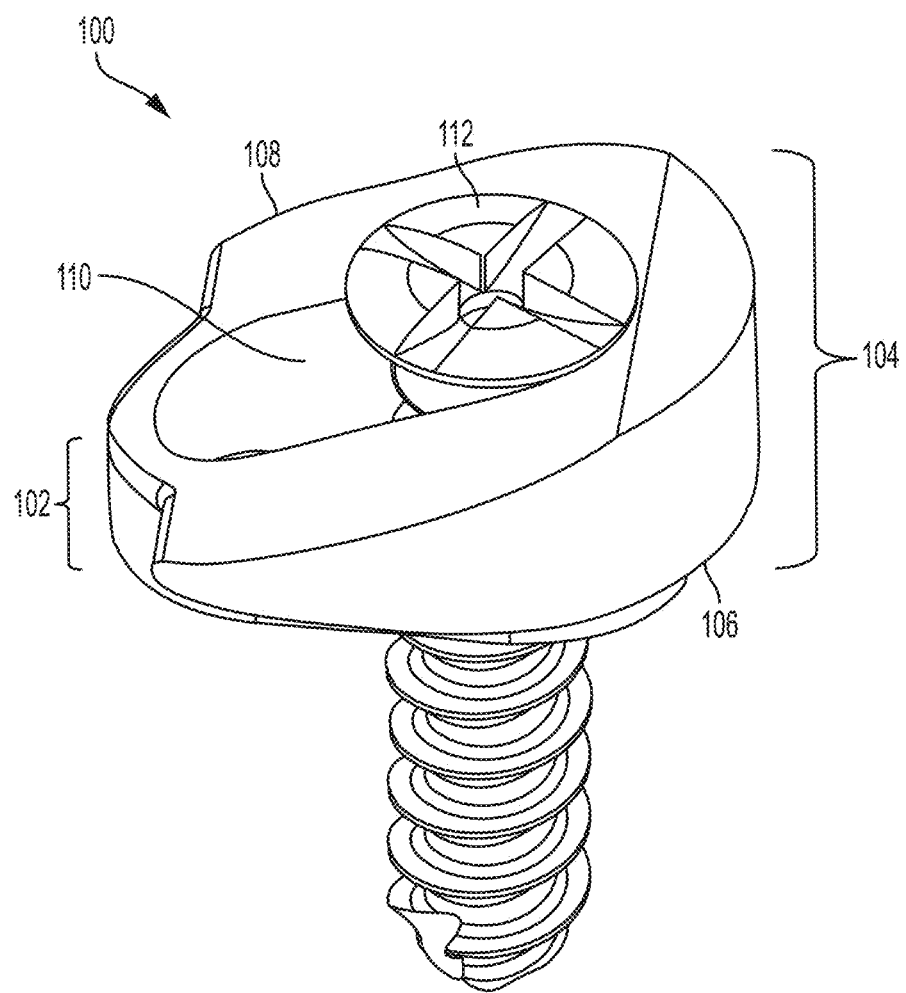
FIG. 6 illustrates a side perspective view of a compression force magnifier with an inserted screw, in accordance with an aspect of the present invention.
Figure 7:
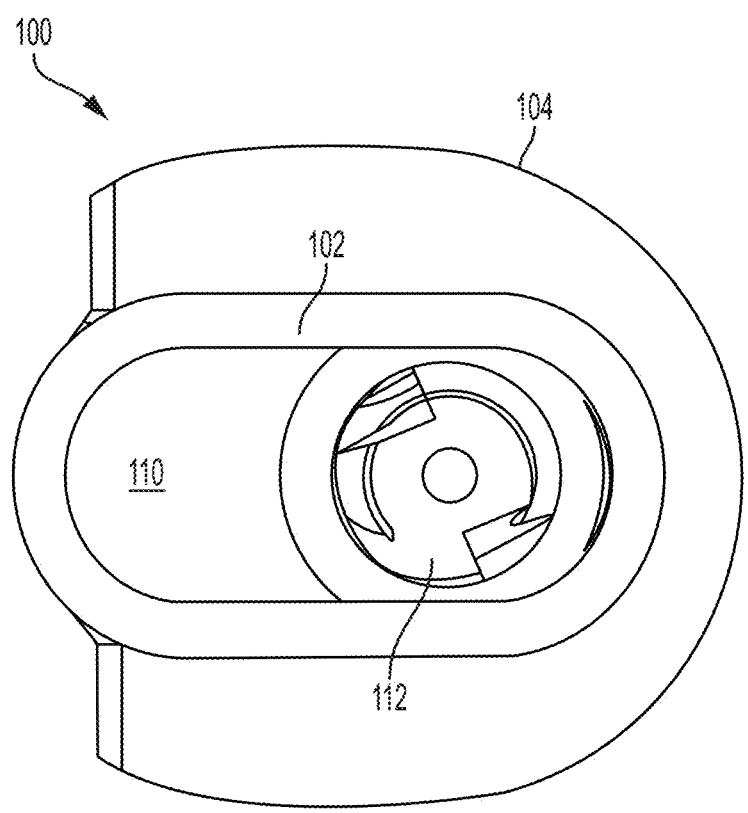
FIG. 7 illustrates a bottom view of a compression force magnifier with an inserted screw, in accordance with an aspect of the present invention.
Figure 8:
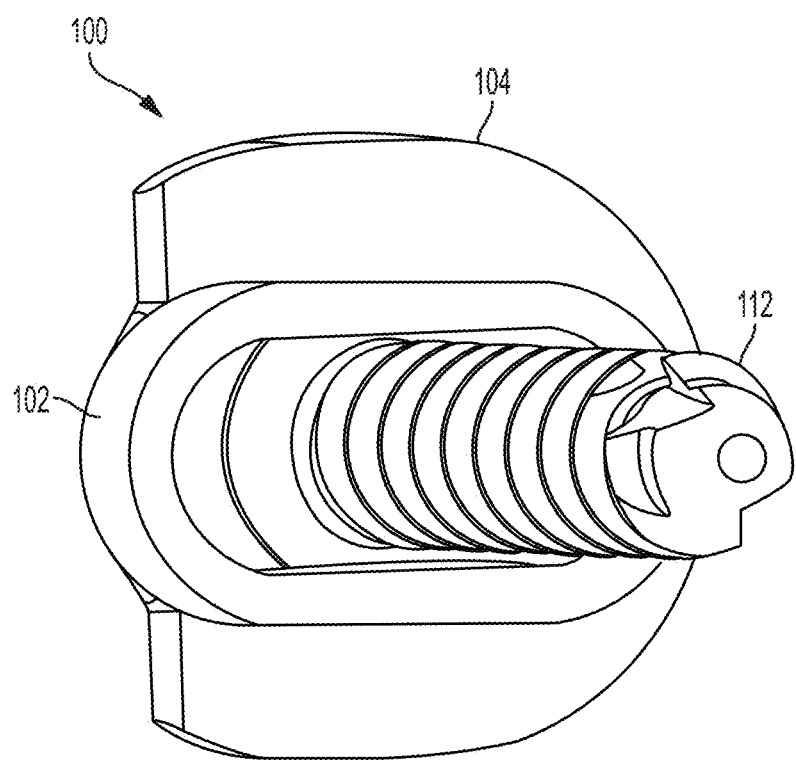
FIG. 8 illustrates a bottom perspective view of a compression force magnifier with an inserted screw, in accordance with an aspect of the present invention.
Figure 9:
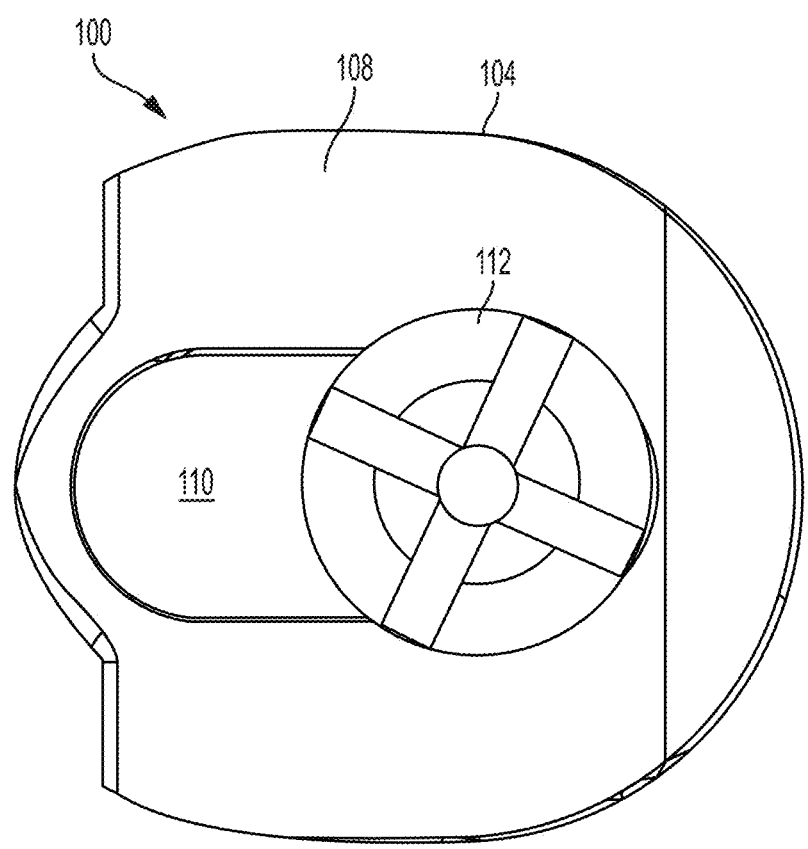
FIG. 9 illustrates a top view of a compression force magnifier with an inserted screw, in accordance with an aspect of the present invention.
Figure 10:
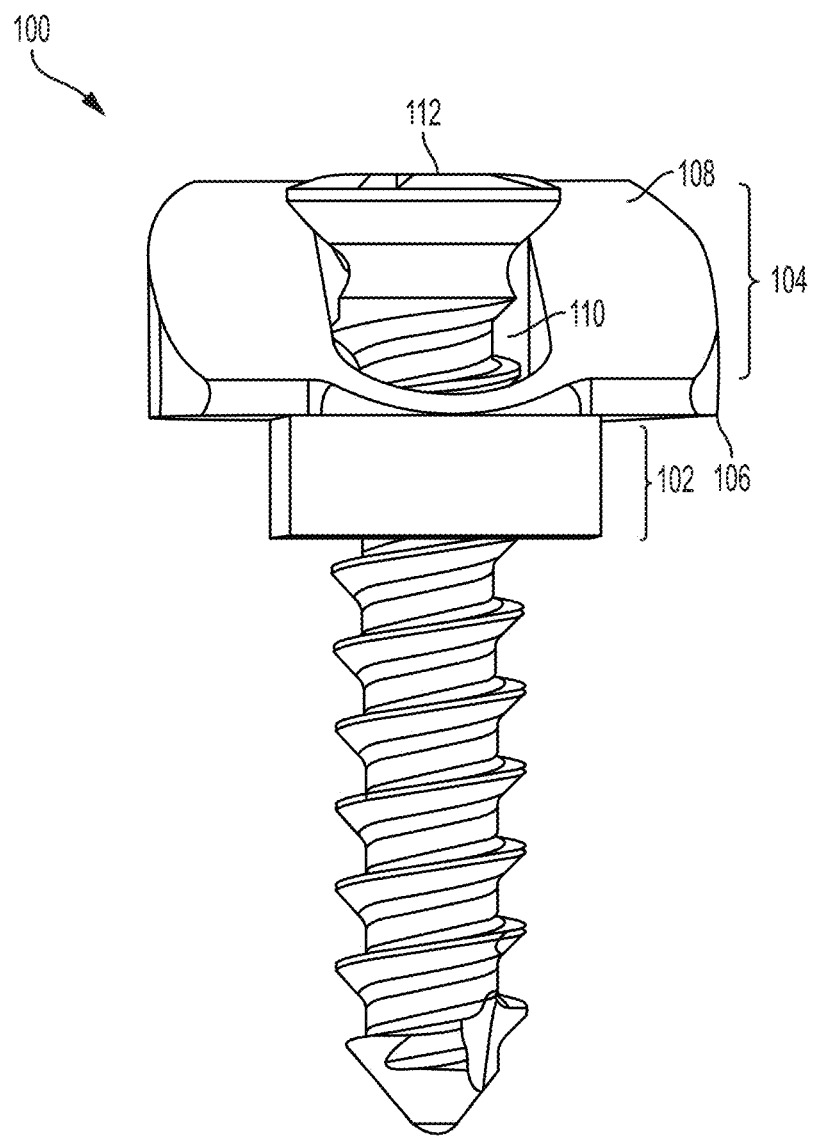
FIG. 10 illustrates a front elevational view of a compression force magnifier with an inserted screw, in accordance with an aspect of the present invention.
Figure 11:
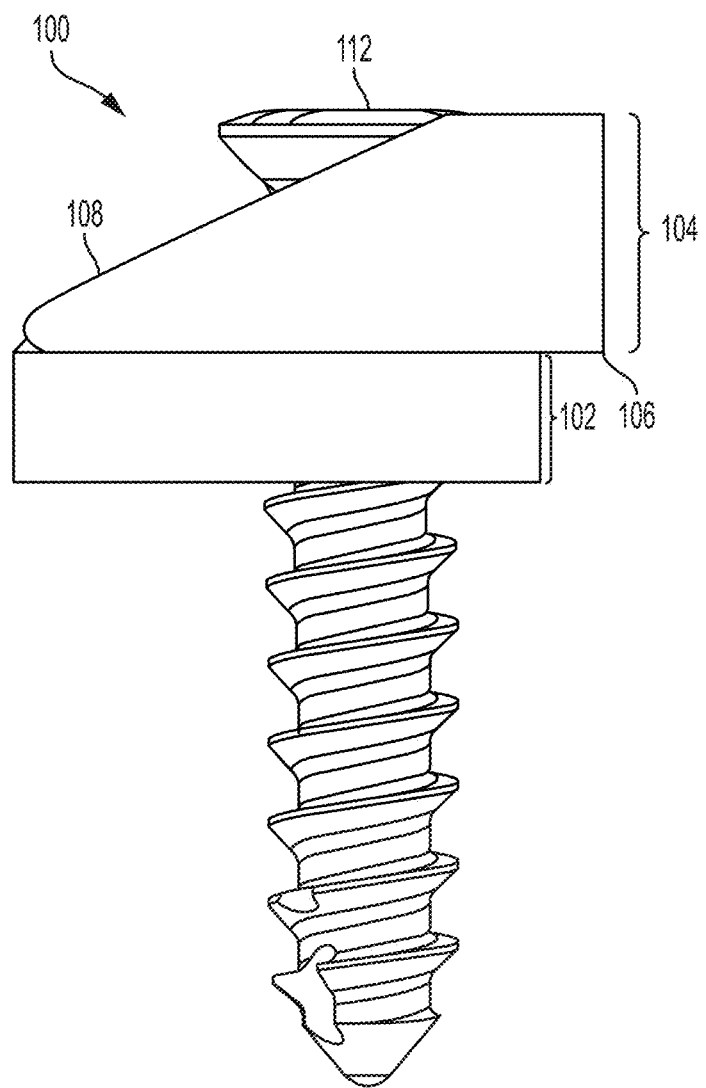
FIG. 11 illustrates a side elevational view of a compression force magnifier with an inserted screw, in accordance with an aspect of the present invention.
Figure 12:
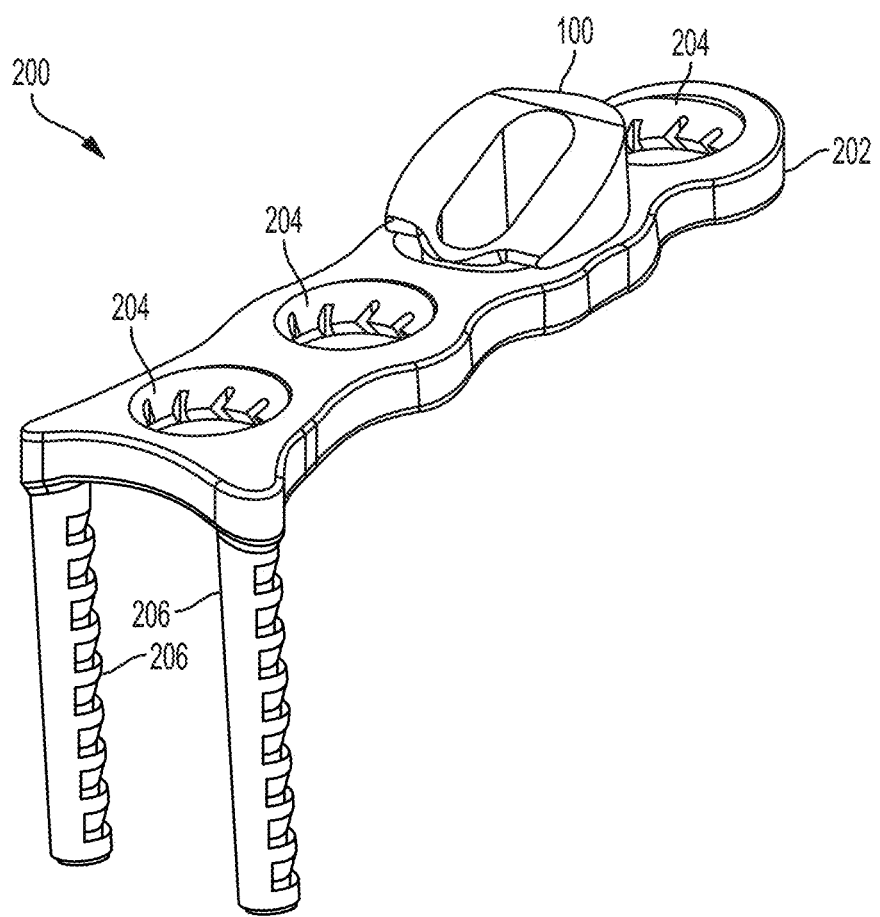
FIG. 12 illustrates a top perspective view of a compression bone plate with an inserted force magnifier, in accordance with an aspect of the present invention.
Figure 13:
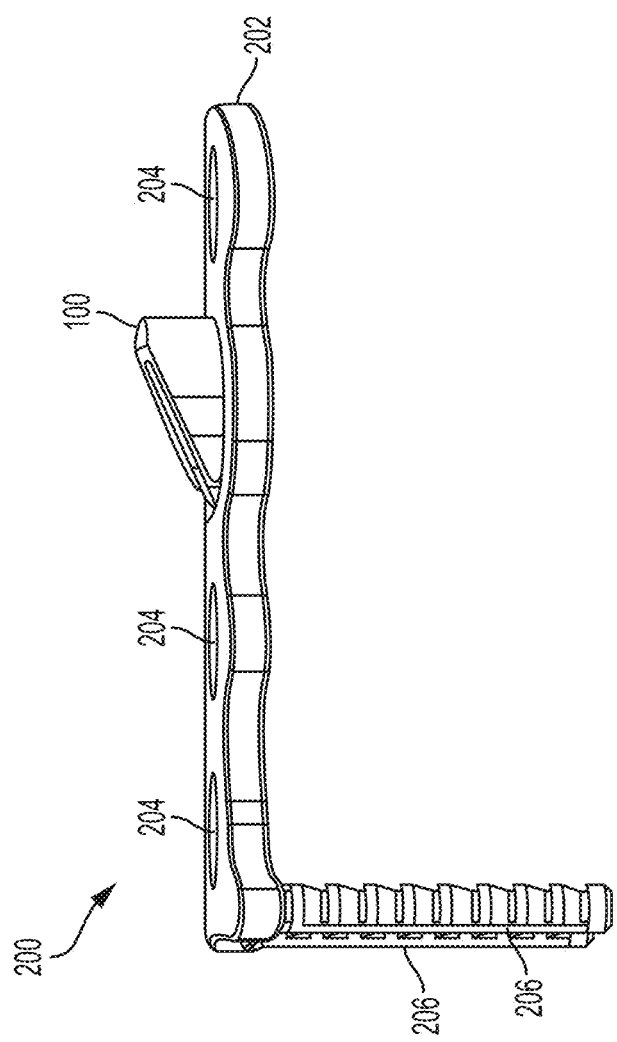
FIG. 13 illustrates a side elevational view of a compression bone plate with an inserted force magnifier, in accordance with an aspect of the present invention.

As shown in FIGS. 1, 2 and 4, the compression force magnifier 100 can include a hole 110 extending vertically through the ramped component 104 and the engaging surface 102 so that an opening extends through the entirety of the compression force magnifier 100. The hole 110, for example, may be an oval shape, defining for example, a slot. As seen in FIG. 6, as a screw is tightened into a bone that sits below a base plate, the screw will translate or move down the ramped component 104 and across the slot, to create a high compressive force through the bone plate, as will be explained in more detail below.

As shown in FIGS. 6-11, the compression force magnifier 100 may be used in conjunction with a threaded device, such as for example, a screw 112 or k-wire (not shown), for attaching to a bone or bone fragment positioned below the coupled bone plate. For instance, when the screw 112 is inserted through the hole 110 at the top of the ramped component 104, as the screw 112 is tightened into the underlying bone, the screw will migrate or move down the ramped component 104, causing the bone to move in a direction parallel to the length of the slot, in some instances drawing one bone closer to another bone or bone fragment through the compressive force applied as the screw descends the ramp. The movement of the screw will draw two bones closer together, but will also apply a larger compressive force by virtue of the height of the ramp and resultant higher created leverage force.

Figure 14:
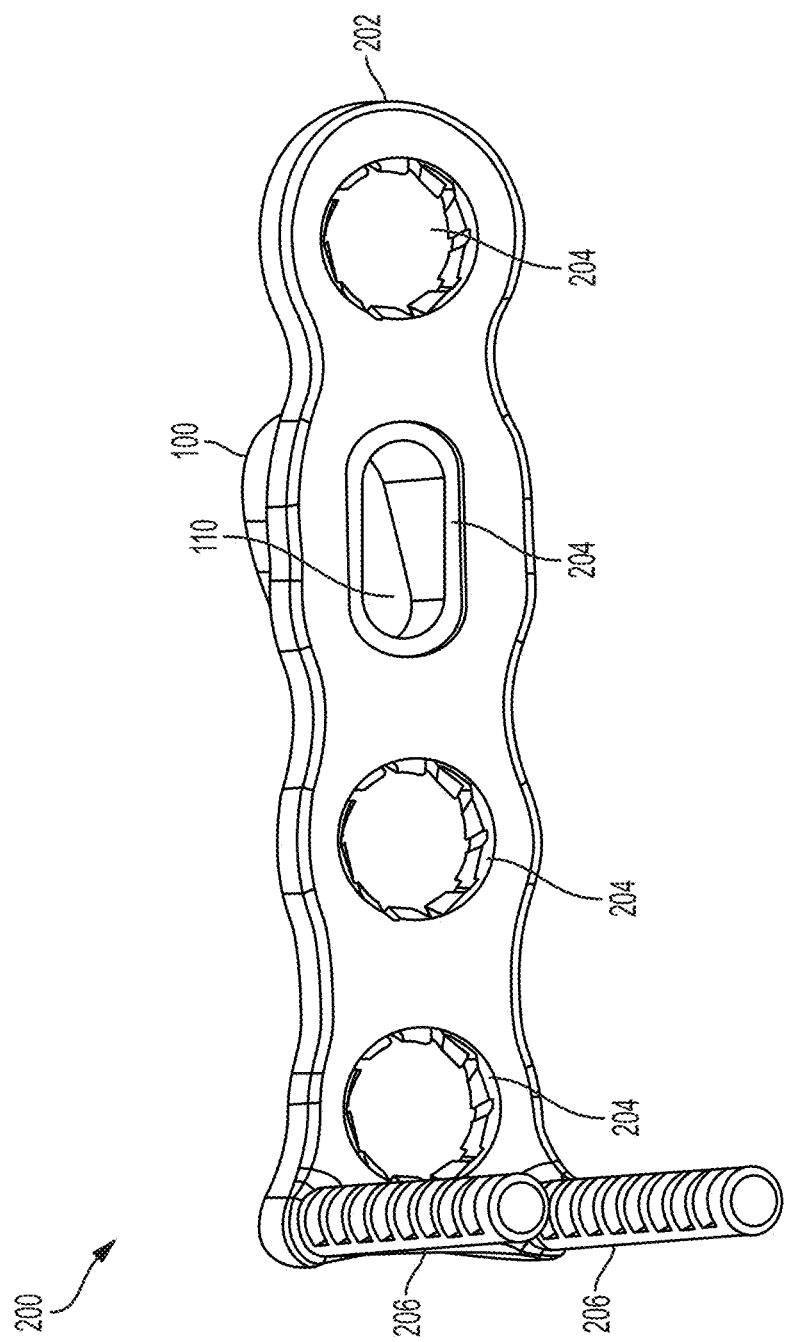
FIG. 14 illustrates a bottom perspective view of a compression bone plate with an inserted force magnifier, in accordance with an aspect of the present invention.
Figure 15:
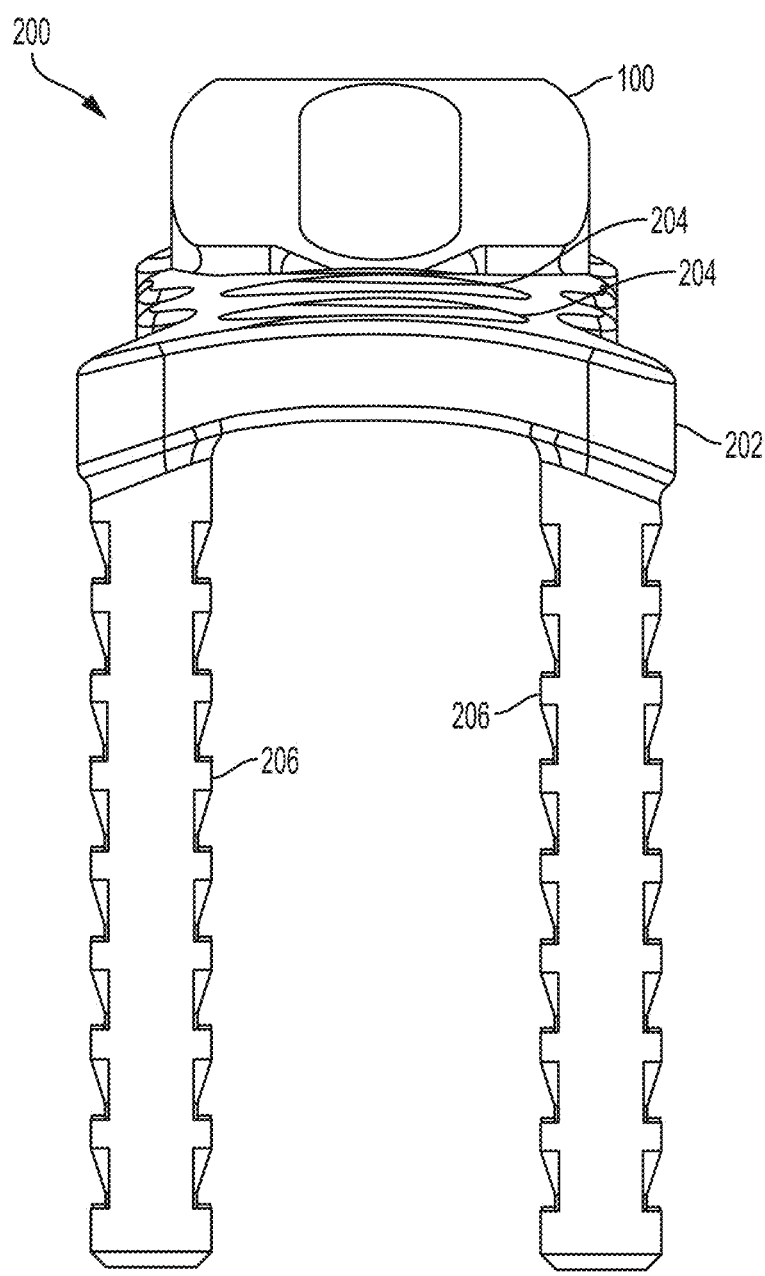
FIG. 15 illustrates a front elevational view of a compression bone plate with an inserted force magnifier, in accordance with an aspect of the present invention.

As shown in FIGS. 12-15, also disclosed is a bone compression assembly 200, which may include for example, a bone plate 202. The bone plate 202 as shown may be an elongate bone plate with a slight medial-lateral curvature as illustrated in FIGS. 12-15, but it can also include step bone plates or other orthogonal designs. The bone plate 202 can include a plurality of screw holes 204 for attaching the bone plate 202 to one or more bones or bone fragments (not shown). Additionally, a set of tines 206, for example, may be included on the bone plate 202 for implantation in a bone or bone fragment. The compression force magnifier 100, as described previously, may be inserted or nested into at least one screw hole 204, and as seen in FIG. 14, the particular screw hole 204 may be configured as a slot to match the engagement surface 102 of the compression force magnifier 100.

Figure 16:
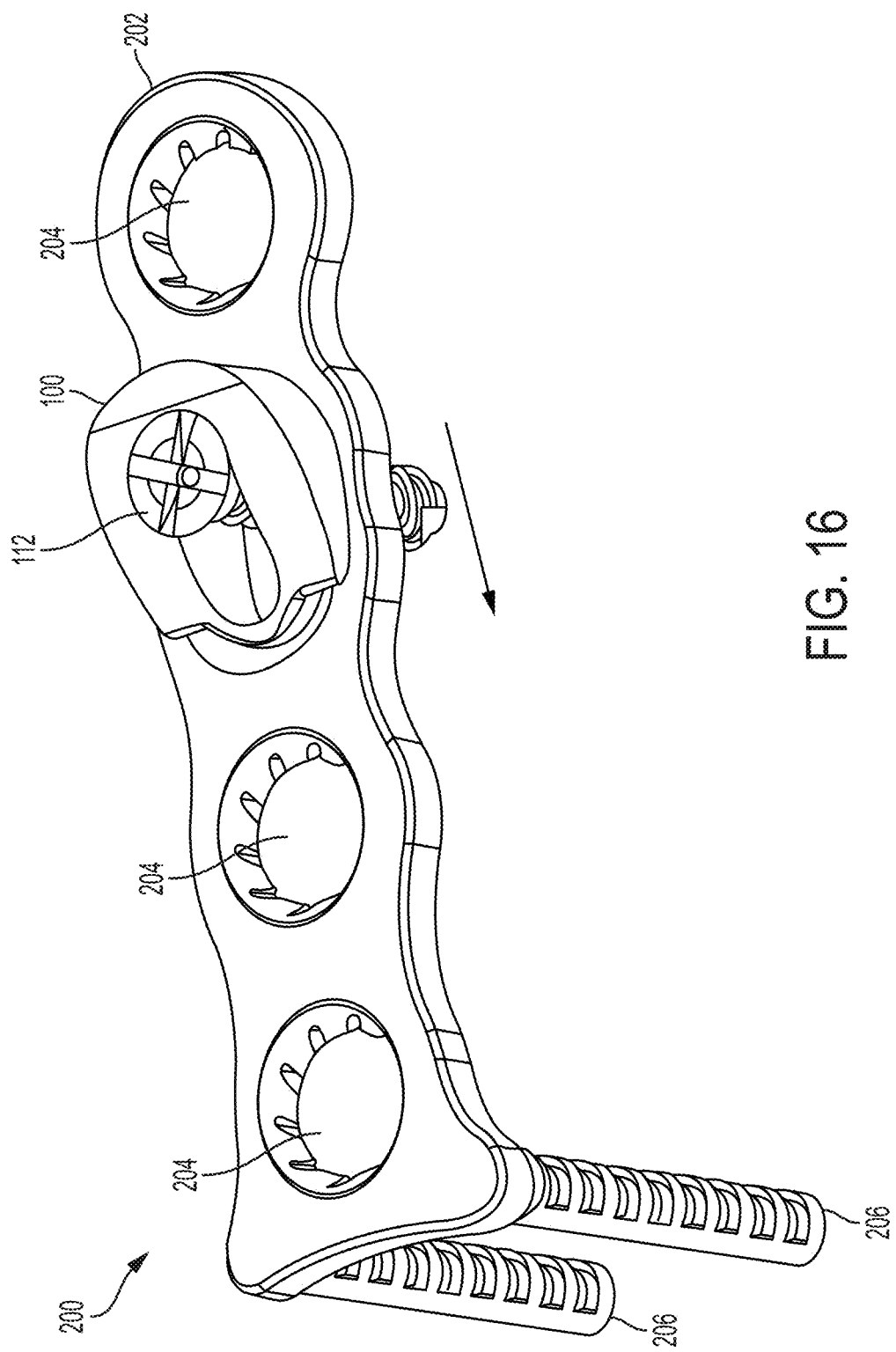
FIG. 16 illustrates a side perspective view of a compression bone plate with an inserted force magnifier and inserted compression screw, in accordance with an aspect of the present invention.
Figure 17:
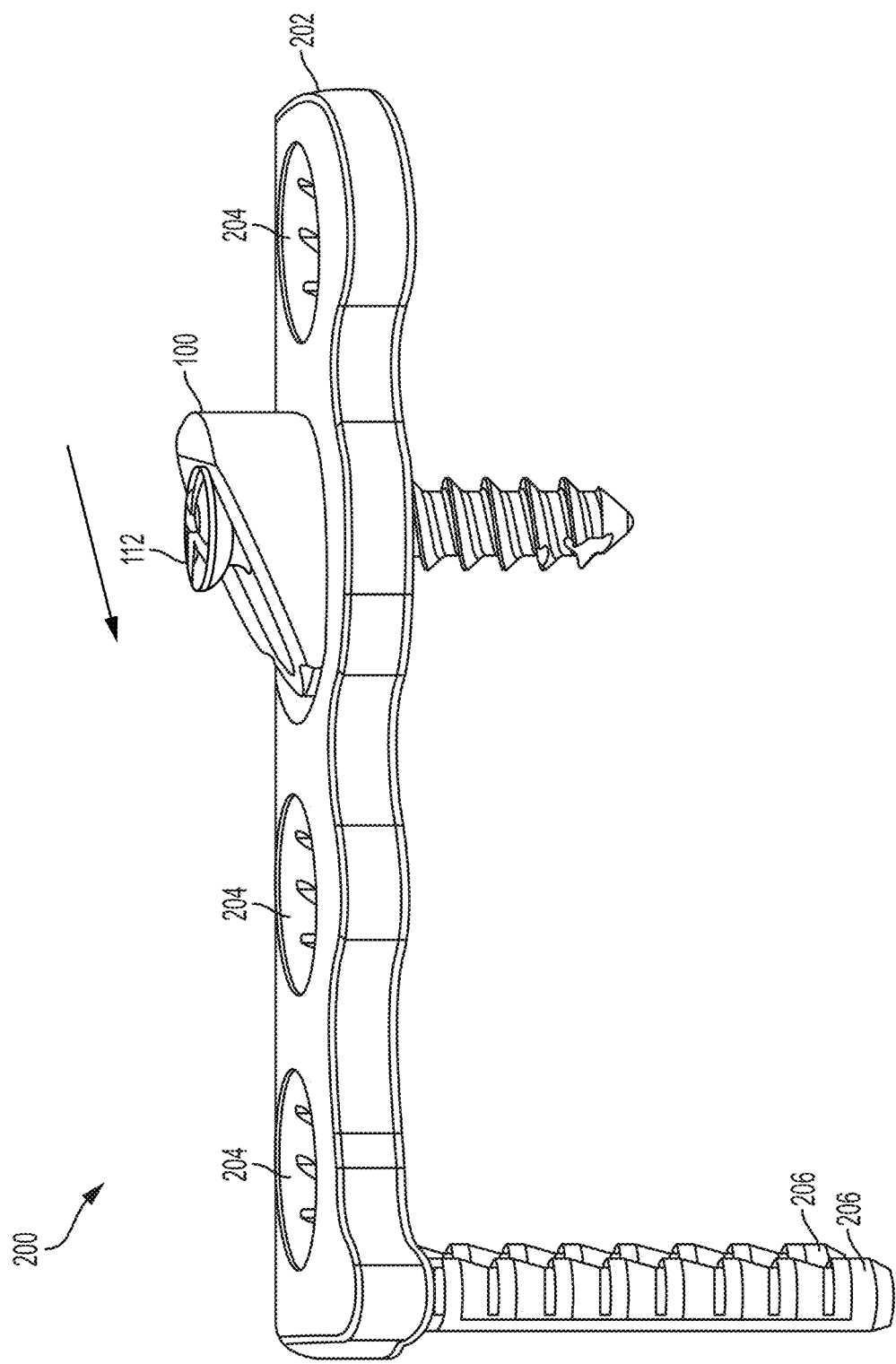
FIG. 17 illustrates a side elevational view of a compression bone plate with an inserted force magnifier and inserted screw, in accordance with an aspect of the present invention.

As seen in FIGS. 16 and 17, similar to FIGS. 6-11, a screw 112 may be used in conjunction with the bone compression assembly 200, to facilitate the movement of two bones and/or fragments closer together. When the screw 112 inserted, it moves down the ramp in the direction indicated by the arrows of FIGS. 16 and 17, moving the second bone a distance D, which may be equal to the length of the slot of hole 110, which pulls the bone and/or fragment below the bone plate 202 closer to a second bone and/or fragment, which is secured to the bone plate 202.

The method, more specifically, of using a bone compression assembly 200 includes attaching a bone plate 202 to a first bone or fragment, for instance on the left side of FIG. 17, using tines 206 or screws or other bone fixation devices, such as compression screws or locking screws, through at least one of the screw holes 204 on the left side of the assembly 200. A compression force magnifier 100 may, before or after attaching the bone plate 202 to a first bone or fragment, be inserted into at least one of the screw holes 204 of the bone plate 202. A first screw 112 may be inserted into and through the compression force magnifier 100 and into a second bone or fragment, for instance, on the right side of the assembly 200. Tightening of the first screw 112 results in a compressive force being applied between the first bone or fragment and the second bone or fragment, as described above. As the screw 112 moves down the ramp the resultant force pulls the second bone on the right side toward the left side of the assembly 200, closer to or into contact with the first bone on the left side of the assembly 200. Any amount of pressure may be applied by continuing to tighten the screw 112 to the end of the ramped surface 108 of the compression force magnifier 100. When the desired amount of movement has been achieved, the bone plate may be more permanently attached to the second bone or fragment, for instance, by inserting a second screw, such as a compression screw or locking screw, into the right most screw hole 204 of the bone plate 202.

Once the second bone or fragment is secured to the bone plate 202, the first screw 112 may be unscrewed and removed, with the bones positions remaining where they were. The compression force magnifier 100 may then be removed utilizing any tool or method necessary to disengage the engaging surface 102 of the compression force magnifier 100. While illustrated with four screw holes 204, the bone plate 202 may include any number of holes, and all or some may be used for securing the bone plate 202 to the first and second bones or bone fragments, depending on the type of joint compression necessary and the size and strength of the bones. Once all of the screw holes to be used have been filled with screws or other fixation devices, the compression force magnifier 100 is removed, and the remaining screw hole, which may be slotted, can be utilized to help further secure the second bone by inserting a third screw or other fixation device, which may have a larger diameter than the first screw, into the hole left in the bone by the first screw 112. For example, the first screw 112 may create a pilot hole for the final screw, which will fit flush in the remaining screw hole/slot. Having the removable compression force magnifier 100, eliminates the clinical problem of resultant proud or protruding screws, which may have happened with previous designs of compression devices which include integrated ramps rather than a removable magnifier 100. In some embodiments, the initial first screw may be between 1 and 2 mm, and the subsequent second screw may be in the range of between 2 and 6.5 mm. The ramp angle and length of the compression force magnifier 100 allows for movement or a translational distance of the second bone/fragment in the range of 1 and 5 mm.

Figure 18:
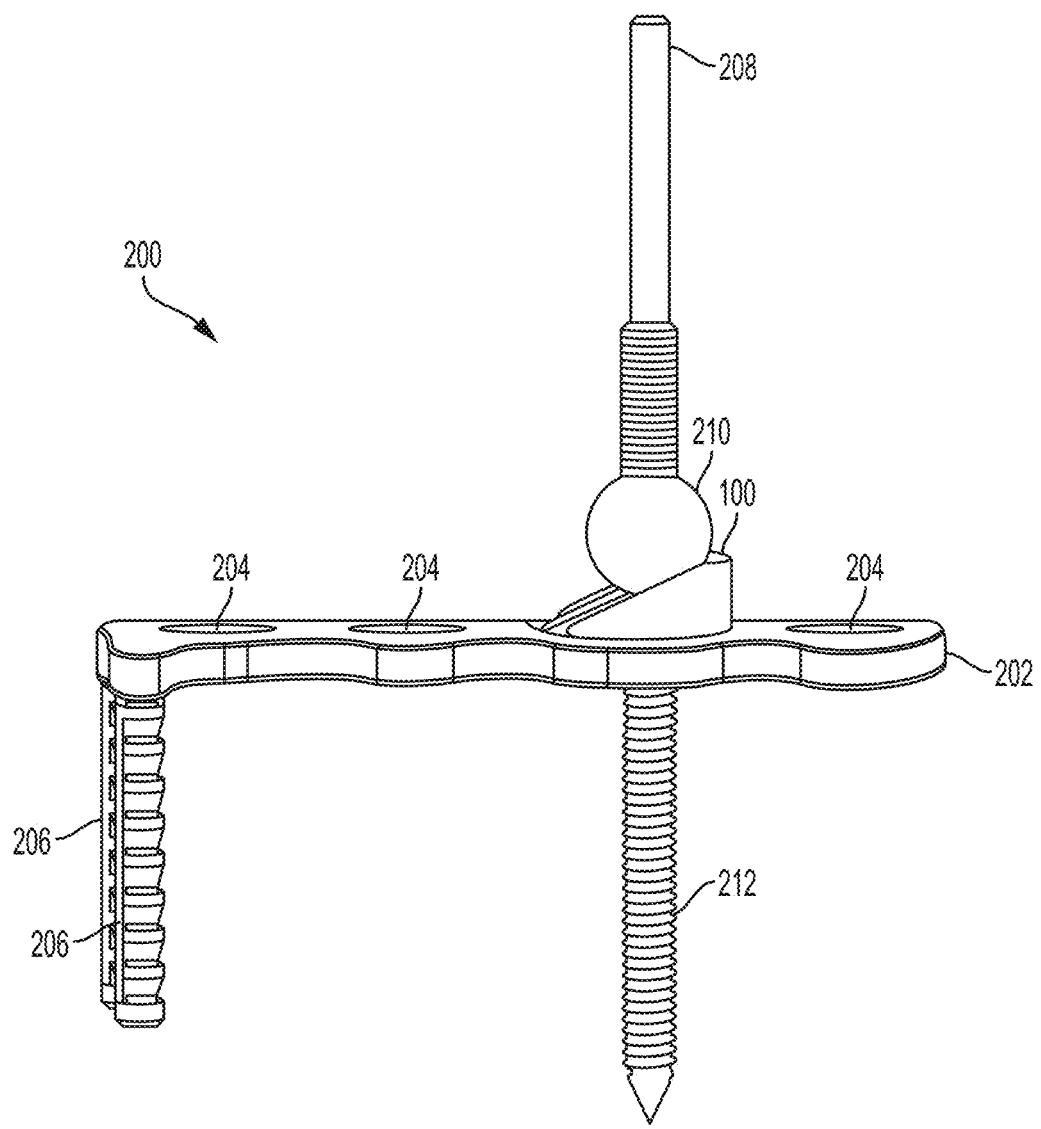
FIG. 18 illustrates a side elevational view of a compression bone plate with an inserted force magnifier and an inserted olive wire, in accordance with an aspect of the present invention.
Figure 19:
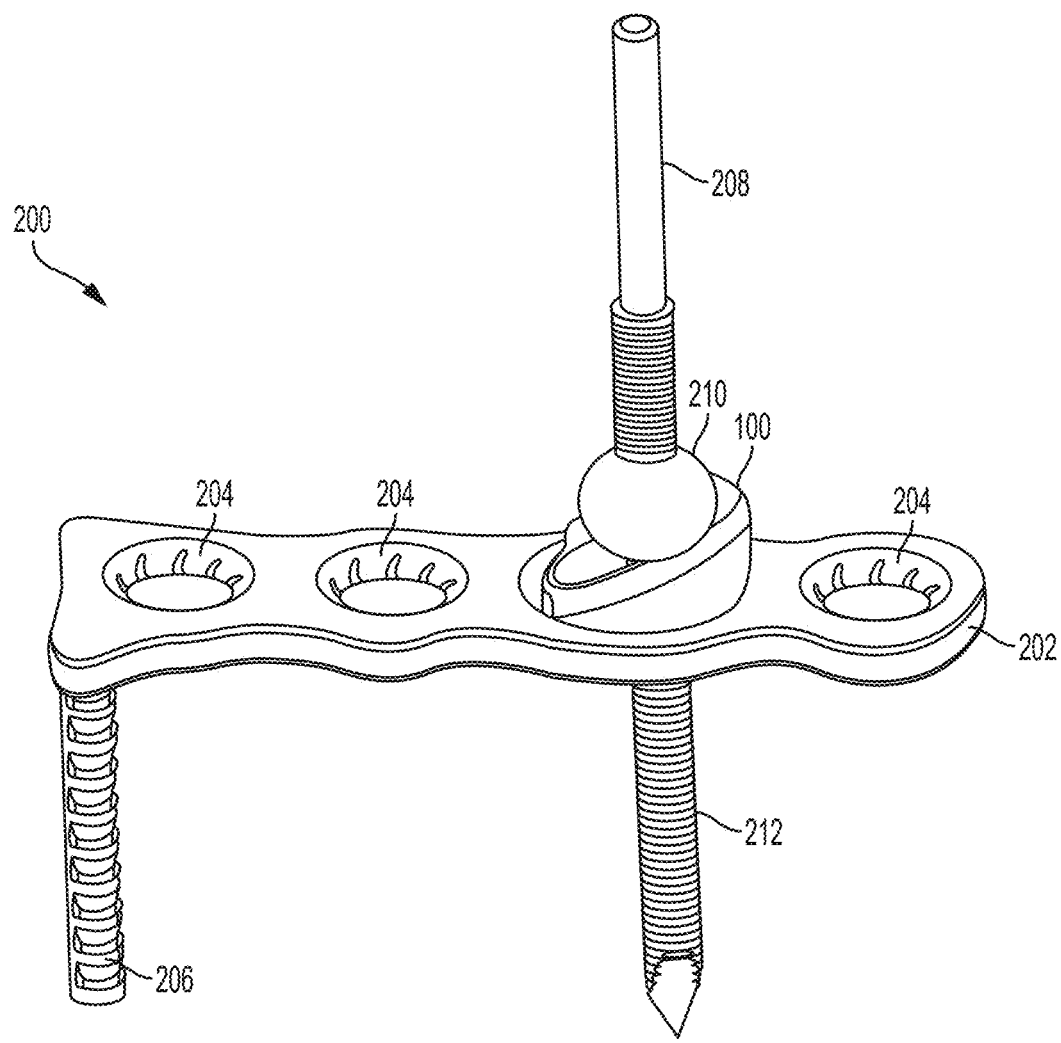
FIG. 19 illustrates a side perspective view of a compression bone plate with an inserted force magnifier and an inserted olive wire, in accordance with an aspect of the present invention.

Although a screw 112 is described as being used in the screw hole 110 of the compression force magnifier 100, in an alternative embodiment, as illustrated in FIGS. 18-19, a threaded olive wire 208 may be utilized, including a ball 210 as opposed to the head of a screw, to translate down the ramped surface. Any olive wires known in the art may be used, and it may include a cancellous screw thread or other compression screw thread 212 on the bottom end of the wire, which like the screw above, may be a smaller diameter than the end screw which will be inserted.

Figure 20:
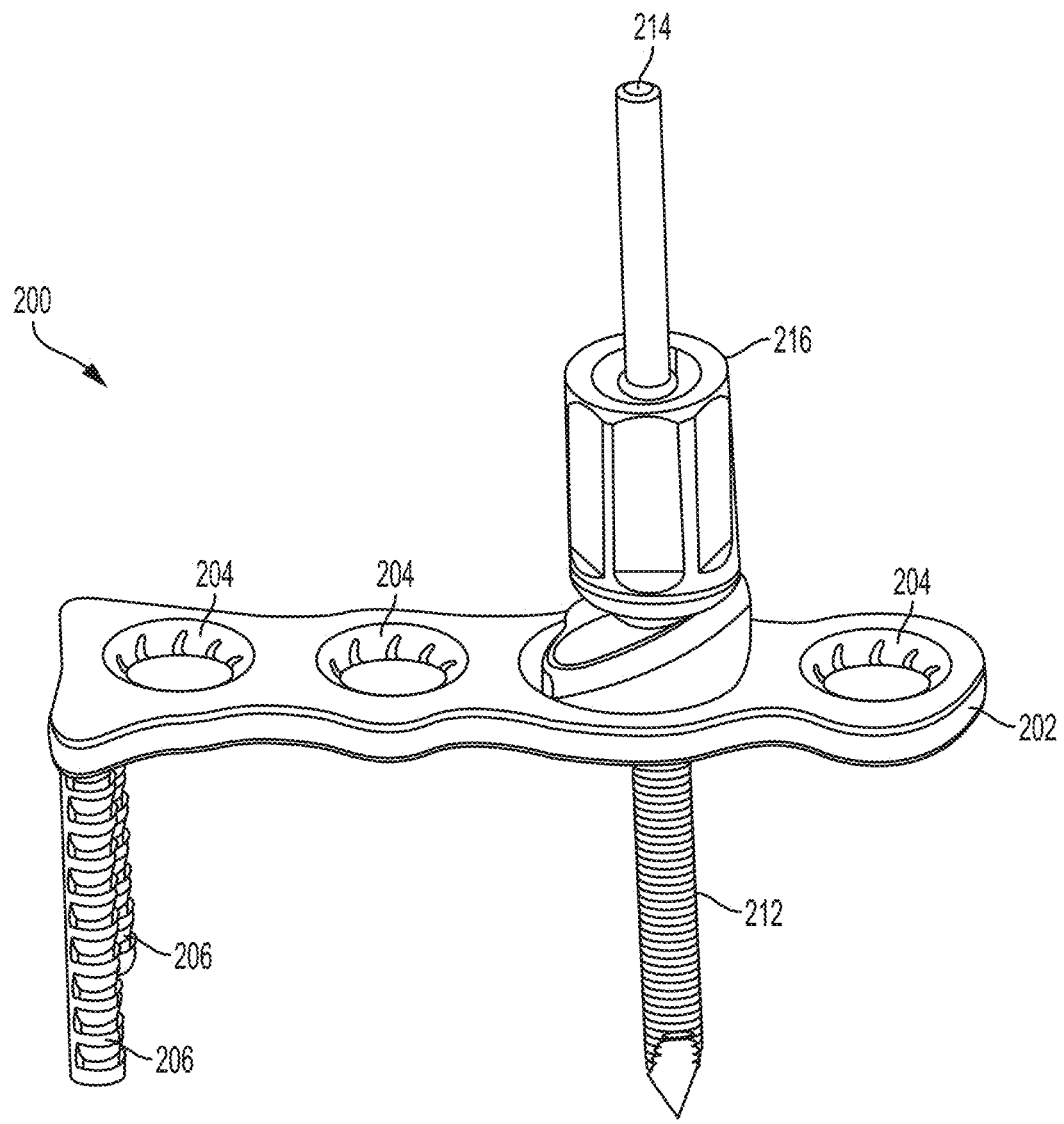
FIG. 20 illustrates a side perspective view of a compression bone plate with an inserted force magnifier and an inserted threaded pin with an engaged nut, in accordance with an aspect of the present invention.

Further, shown in FIG. 20 is another alternative embodiment to the screw 112, which may include a threaded pin 214 including a cancellous screw thread or other compression screw thread 212 on the bottom end of the pin 214. A nut 216 or similar threaded member may be utilized to engage the threaded top portion of pin 214. The nut 216 would migrate down the ramp of the compression force magnifier 100 as it is threaded onto the threaded pin, to create and apply the compression force between the two bones.

Figure 21:
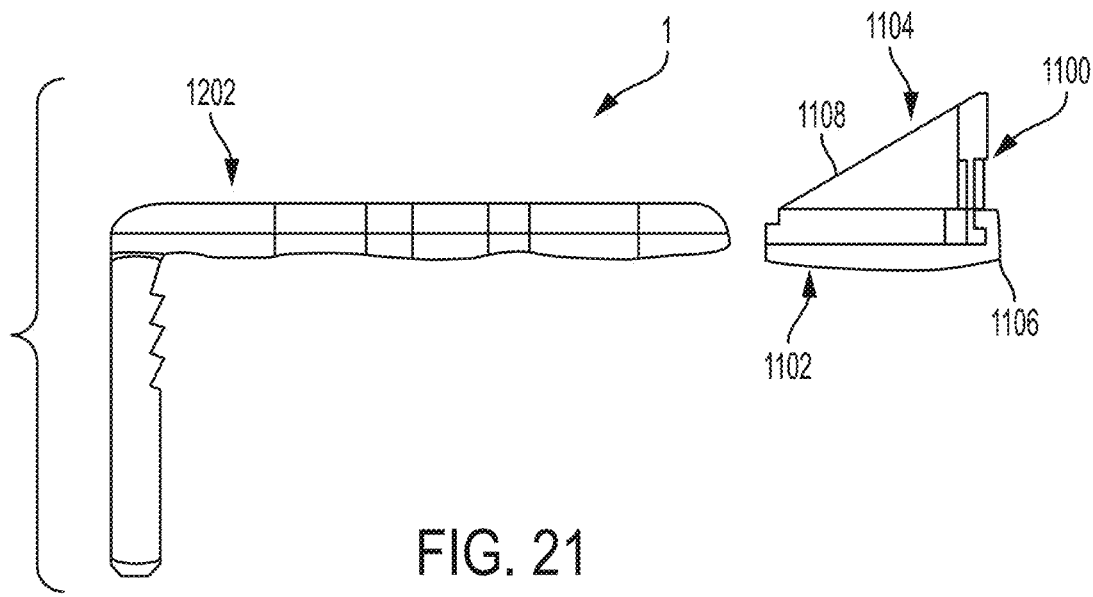
FIG. 21 illustrates a side disassembled view of an alternative embodiment of a compression bone plate with a force magnifier in accordance with an aspect of the present invention.
Figure 22:
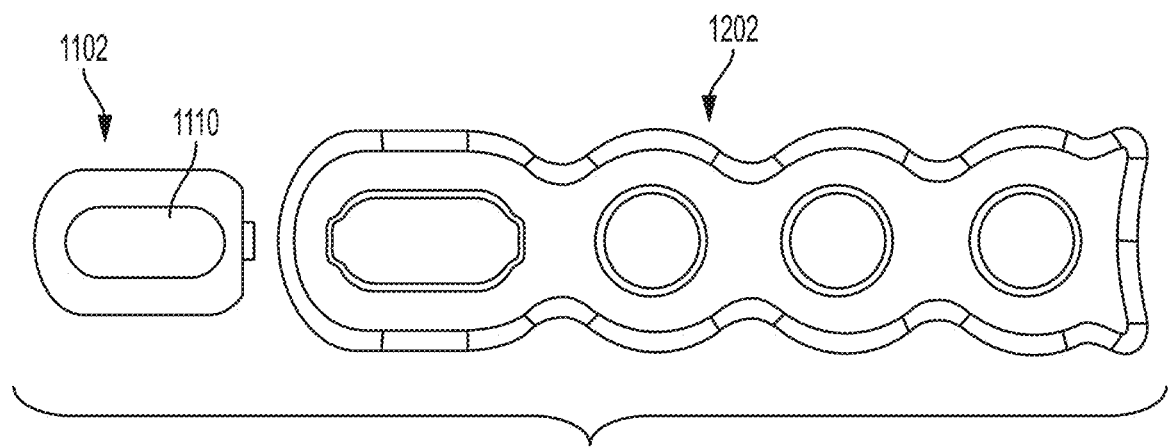
FIG. 22 illustrates a top disassembled view of an alternative embodiment of a compression bone plate with a force magnifier in accordance with an aspect of the present invention.
Figure 23:
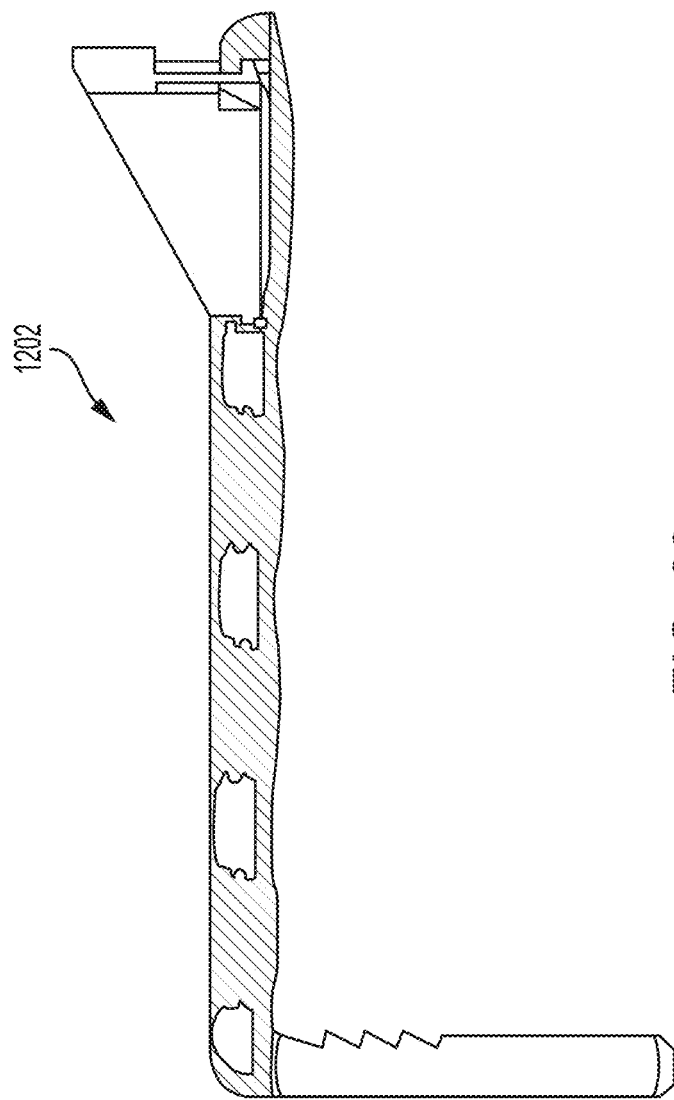
FIG. 23 illustrates a side assembled view of an alternative embodiment of a compression bone plate with a force magnifier in accordance with an aspect of the present invention.

FIGS. 21-23 illustrate a side disassembled view, a top disassembled view, and a side assembled view, respectively of an alternative embodiment of a compression bone plate 1202 with a force magnifier 1100. As shown in FIGS. 21-23, the compression force magnifier 1100 may also include a ramped component 1104 positioned above the engaging surface 1102. For instance, the ramped component 1104 may include a flat bottom surface 1106 immediately adjacent to the engaging surface 1102 for sitting against a surface of a bone plate. The ramped component may also include a pitched, or angled, upper surface 1108, creating a ramped surface, the angle of which may vary for example from 1 to 89 degrees, but more preferably in the range of 20 to 55 degrees with a height range for example of generally 1.5 to 5 millimeters.

As shown in FIGS. 21-23, the compression force magnifier 1100 can include a hole 1110 extending vertically through the ramped component 1104 and the engaging surface 1102 so that an opening extends through the entirety of the compression force magnifier 1100. Tht: hult: 1110, for example, may be an oval shape, defining for example, a slot. In the same manner shown in FIG. 6, as a screw is tightened into a bone that sits below a base plate, the screw wi II translate or move down the ramped component 1104 and across the slot, to create a high compressive force through the bone plate, as will be explained in more detail below.

As shown in FIG. 23, bone compression assembly 1200 includes bone plate 1202. The bone plate 1202 as shown may be an elongate bone plate with a slight medial-lateral curvature as illustrated in FIGS. 12-15, but it can also include step bone plates or other orthogonal designs. The bone plate 1202 can include a plurality of screw holes 1204 for attaching the bone plate 1202 to one or more bones or bone fragments (not shown). Additionally, a set of tines 1206, for example, may be included on the bone plate 1202 for implantation in a bone or bone fragment.

The compression force magnifier 1100, as described previously, may be inserted or nested into at least one screw hole 204, and as seen in FIG. 21, the particular screw hole 1204 may be configured with cutouts to match corresponding flexible tabs on compression force magnifier 1100 as an alternative means for connecting the two components.

Figure 24:
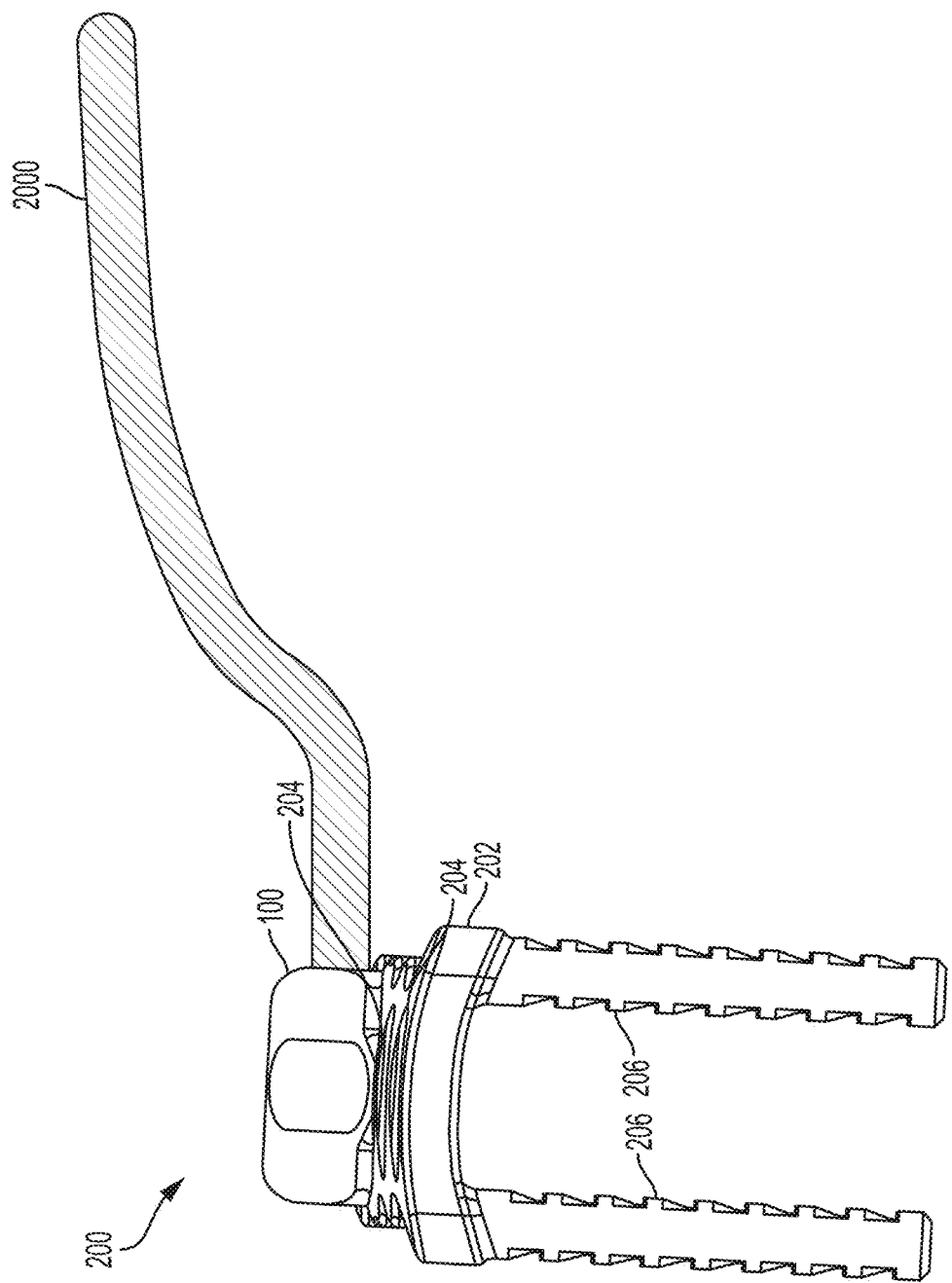
FIG. 24 illustrates a top view of a handle for use as a force magnifier for a compression bone plate in accordance with an aspect of the present invention.
Figure 25:
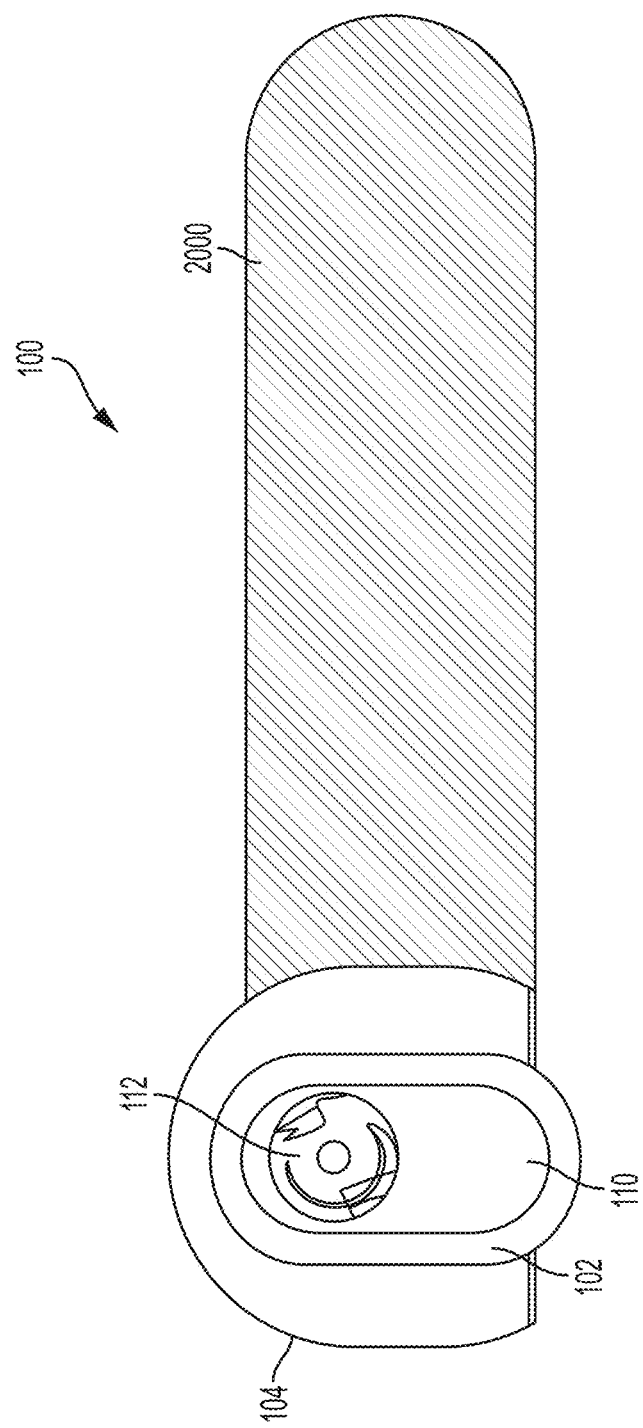
FIG. 25 illustrates a top view of a handle for use as a force magnifier for a compression bone plate in accordance with an aspect of the present invention.

FIGS. 24 and 25 illustrate a side and top view respectively of a handle 2000 for use as a force magnifier for a compression bone plate in accordance with an aspect of the present invention. As illustrated in FIGS. 24 and 25, handle 2000 may incorporate the features of compression force magnifier 100 or 1100 to provide addition compression to a bone plate 202 or 1202.

It is to be understood that the above description is intended to be illustrative, and not restrictive. Numerous changes and modification3 may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description; it is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for use in bone compression, the method comprising:
    attaching a bone plate to a first bone;
    inserting a compression force magnifier into an opening of a top surface of the bone plate, the opening comprising an elongated slot;
    inserting a first screw through the compression force magnifier and into a second bone to apply a compressive force between the first bone and the second bone; and
    inserting a second screw through a hole in the bone plate into the second bone to secure the first bone and the second bone.

2. The method of claim 1 further comprising removing the first screw and the compression force magnifier from the bone plate.

3. The method of claim 2 further comprising inserting a third screw, larger than the first screw, into a hole left by the first screw.

4. The method of claim 1 wherein the compression force magnifier comprises:
    a vertical axis;
    a ramped portion having a ramp surface sloped at a predetermined angle relative to said vertical axis;
    an engaging portion having a distal engaging surface disposed opposite said ramp surface, said engaging portion connected to said ramped portion; and
    a bore extending from said ramp surface through said distal engaging surface.

5. The method of claim 4 wherein the inserting the first screw through the compression force magnifier comprises the first screw contacting the ramp surface to apply the compressive force.

6. The method of claim 4 wherein the ramp surface comprises opposite inner sides bounding the bore.

7. The method of claim 4 wherein said ramped portion has a lower contacting surface extending laterally relative to a longitudinal dimension of said plate above said plate proximal surface and away from said engaging portion.

8. The method of claim 1 wherein the first screw consists of a threaded wire threadably engaged with a threaded member, and further comprising the threaded member being threaded on the wire to contact the ramp surface to apply the compression force.

9. The method of claim 1 wherein the first screw consists of a threaded pin threadably engaged with a nut, and further comprising the nut being threaded on the pin to contact the ramp surface to apply the compression force.

10. A compression force magnifier, said compression force magnifier comprising:
    a vertical axis;
    a ramped portion having a ramp surface sloped at a predetermined angle relative to said vertical axis;
    an engaging portion having a distal engaging surface disposed opposite said ramp surface, said engaging portion connected to said ramped portion;
    a bore, said bore extending from said ramp surface through said distal engaging surface;
    said ramp surface comprising opposite inner sides bounding said bore; and
    said engaging portion receivable in an aperture of a bone plate between a plate proximal surface and a bone contacting surface to releasably attach said engaging portion to said bone plate such that said ramped portion has a lower contacting surface extending laterally relative to a longitudinal dimension of the plate above the plate proximal surface of the plate and away from said engaging portion.

11. A bone compression assembly apparatus, said assembly apparatus comprising:
- a bone plate, said plate having a plate proximal surface and a bone contacting surface disposed opposite said plate proximal surface, said bone plate further comprising an aperture disposed through said plate between said plate proximal surface and said bone contacting surface, said aperture having a longitudinal axis; and
- a compression force magnifier, said compression force magnifier comprising:
  - a vertical axis;
  - a ramped portion having a ramp surface sloped at a predetermined angle relative to said vertical axis;
  - an engaging portion having a distal engaging surface disposed opposite said ramp surface, said engaging portion connected to said ramped portion, said ramped portion Navin a lower contacting surface extending laterally relative to a longitudinal dimension of said plate above said plate proximal surface and away from said engaging portion;
  - a bore, said bore extending from said ramp surface through said distal engaging surface;
  - said compression force magnifier releasably attached to said bone plate such that said engaging portion is received in said aperture;
- a first threaded member disposed through said bore and said aperture and adapted to be inserted into a bone, said first threaded member engaged with a second threaded member to allow the second threaded member be threaded on the first threaded member to contact the ramp surface to apply a compression force when the first threaded member is connected to the bone.

12. The bone compression assembly apparatus of claim 11 wherein said first threaded member consists of a threaded wire.

13. The bone compression assembly apparatus of claim 11 wherein said first threaded member consists of a threaded pin and said second threaded member comprises a nut.

14. The bone compression assembly apparatus of claim 11 wherein said ramp surface comprises opposite inner sides bounding said bore.

15. The bone compression assembly apparatus of claim 11, wherein the aperture in the bone plate comprises an elongated slot.

* * * * *